United States Patent [19]

Breyen et al.

[11] Patent Number: 5,423,881
[45] Date of Patent: Jun. 13, 1995

[54] MEDICAL ELECTRICAL LEAD

[75] Inventors: Mark D. Breyen, Plymouth; Joseph F. Lessar, Coon Rapids; Kenneth B. Stokes, Brookyn Park; James E. Upton, New Brighton; Naim S. Istephanous, Roseville; Jennifer P. Miller, Elk River, all of Minn.

[73] Assignee: Medtronic, Inc., Minneapolis, Minn.

[21] Appl. No.: 212,078

[22] Filed: Mar. 14, 1994

[51] Int. Cl.$^6$ .............................................. A61N 1/05
[52] U.S. Cl. .................................. 607/122; 607/115; 128/642
[58] Field of Search ................. 128/642; 607/116-132

[56] References Cited

U.S. PATENT DOCUMENTS

| 4,154,050 | 3/1979 | Nation | 57/200 |
| 4,355,647 | 10/1982 | Heidjann et al. | 130/24 |
| 4,860,446 | 8/1989 | Lessar et al. | 29/858 |
| 4,947,866 | 8/1990 | Lessar et al. | 128/784 |
| 5,040,544 | 8/1991 | Lessar et al. | 128/784 |

OTHER PUBLICATIONS

*A Guide to Cardiac Pacemakers*, Chapter 6–Lead Atlas, by Victor Parsonnet, M.D. and Todd Rogers, 1983, pp. 349-443, Philadelphia Pa., F. A. Davis Co.
*Materials Aspects of Implantable Cardiac Pacemaker Leads*, Medical Progress Through Technology,, by Stephen D. Bruck & Edward P. Mueller, Martinus Nijhoff Publishers, Boston, 13:149-160 (1988).
*New Pacing Lead Conductors*, by J. E. Upton, Medtronic, Inc., Minnesota, published in World Symposium on Cardiac Pacing, 6th, Montreal, 1979. Cardiac Pacing-State of the Arts, 1979: Proceedings, Montreal Que.: Pacesymp, 1979, Chapter 29, pp. 6-9.
*Drawn Brazed Strand Conductors for Medtronic Pacing Leads*, by Jim Upton, Medtronic, Inc., 1981.

Primary Examiner—William E. Kamm
Assistant Examiner—Marianne Parker
Attorney, Agent, or Firm—Daniel W. Latham; Harold R. Patton

[57] ABSTRACT

A medical electrical lead of the type which includes an electrode at a distal end of the lead a connector at a proximal end of the lead and an elongated electrical conductor extending between the electrode and the connector. The conductor is comprised of a wire wound in a coil configuration with the wire comprised of a duplex titanium alloy. Materials of such composition have been found to have suitable conductivity for use with implantable pulse generators and suitable fatigue strength when used in endocardial lead placement. Moreover, such materials have been found to pass tests intended to detect metal ion oxidation (MIO) in susceptible polymeric materials.

9 Claims, 2 Drawing Sheets

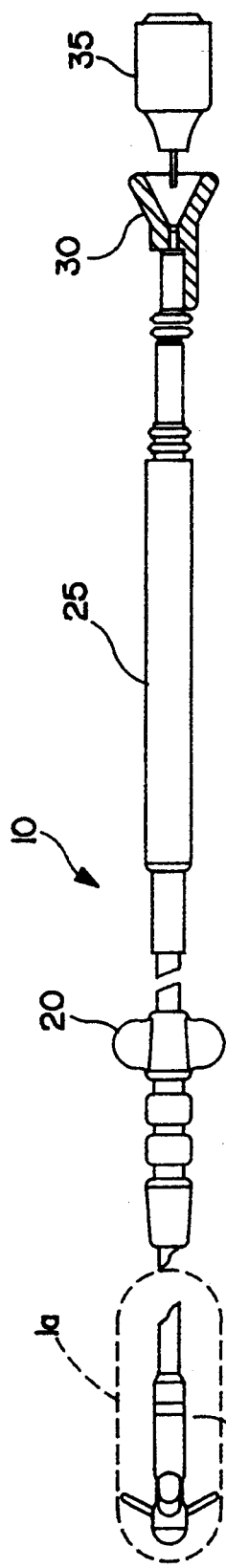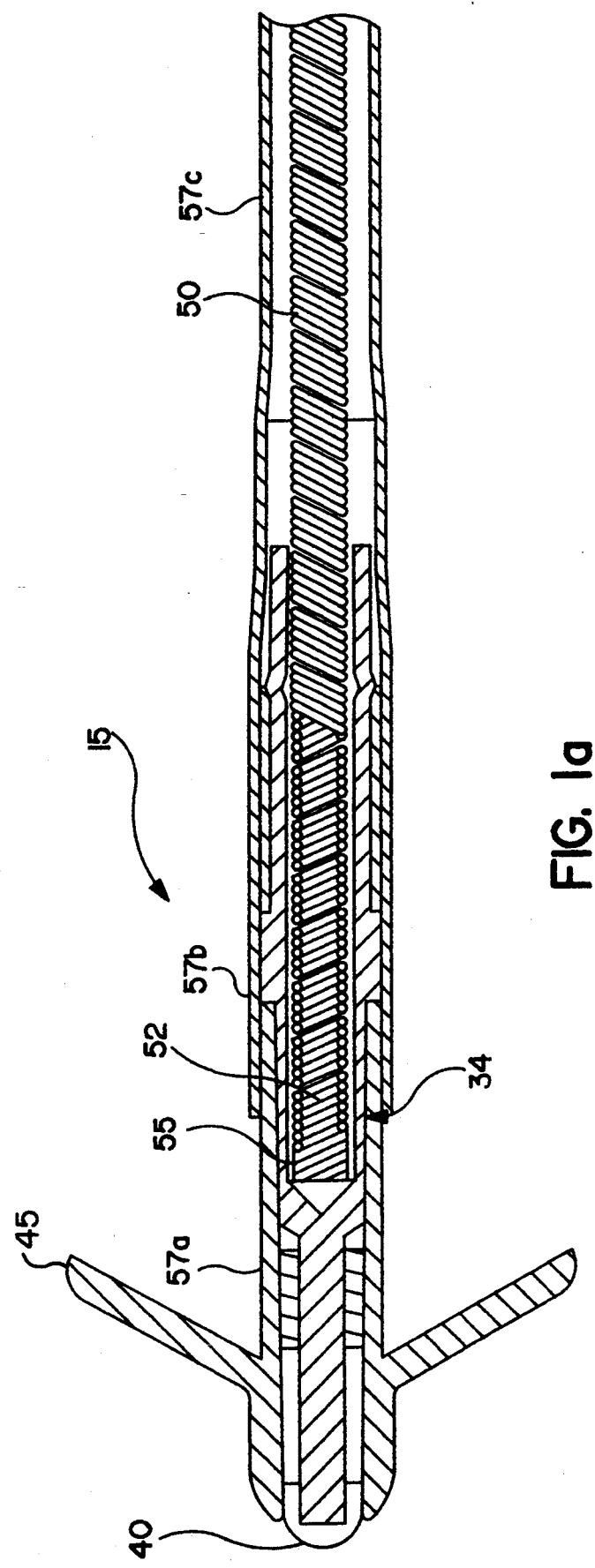

MEDICAL ELECTRICAL LEAD

BACKGROUND OF THE INVENTION

The present invention relates to medical electrical leads and, in particular, to conductors for such leads.

Early cardiac pacemaker conductors were composed of numerous fine, stranded stainless steel wires. Marked improvement in both fracture rate and flexibility resulted when stainless steel conductors were wound into small coils with a hollow core. The hollow core of the coils also improved implantation since a stylet could be passed through the core during implantation to stiffen the lead. Corrosion resistance was significantly increased when stainless steel was replaced with more corrosion-resistant platinum-iridium and nickel alloy materials such as MP35N. Highly specialized conductors were used with such materials such as the use of multifilar wire coils (to avoid loss of electrical continuity in the event that one wire breaks) and drawn brazed strand (DBS) wire material (to provide a low electrical resistance in a wire of high fatigue strength). Multifilar coils can also be used in side-by-side or coaxial arrangements with insulation separating the conductors to provide individual conductors for the transmission of separate signals or stimulation pulses. However, it has been noted that polymeric materials (such as polyether urethanes) used for lead insulation can be adversely affected over long periods of implantation by metal ions from the nickel alloy conductors. Accordingly, it would be desirable to replace nickel alloy conductors like MP35N with other conductors which would not exhibit such a problem.

Of critical importance in this effort is to find a wire material that can be used in a multifilar coil wire geometry that will not fail under the mechanical stresses to which the lead will be subjected. The motions an implanted lead can experience are tension, twist and bending within the coil wire. Each of these produce either normal (tensile or compressive) or shear stresses which occur in all directions, but certain directions predominate depending on the modes of motion involved. If the magnitude of these stresses are too great with respect to the fatigue strength of the material, the structure will fail. Also of great importance is to find a wire material that will provide low electrical resistance and corrosion resistance. Titanium has been suggested as a lead conductor in U.S. Pat. No. 4,355,647 issued to Kallok et al. Titanium is known for its inertness to many corrosive environments. For this reason, titanium has also been mentioned in U.S. Pat. Nos. 5,040,544, 4,947,866 and 4,860,446 issued to Lessar et al as a suitable material for sputter coating onto nickel alloy lead conductors to reduce the release of harmful ions. However, it has not been clear which, if any, alloys of titanium could be used for lead conductors.

It is therefore an object of the invention to provide a medical electrical lead having a titanium alloy conductor material that will not promote the degradation of adjacent polymeric materials.

It is also an object of the invention to provide a medical electrical lead having a titanium alloy conductor material with good fatigue strength when used in a coil geometry.

It is also an object of the invention to provide a medical electrical lead having a titanium alloy conductor material with low electrical resistance.

SUMMARY OF THE INVENTION

These and other objects are accomplished by the medical electrical lead of the present invention. We have discovered a medical electrical lead of the type which includes an electrode at a distal end of the lead a connector at a proximal end of the lead and an elongated electrical conductor extending between the electrode and the connector. The conductor is comprised of a wire wound in a coil configuration with the wire comprised of a duplex titanium alloy. The duplex titanium alloy composition includes percentages of alpha stabilizers such as aluminum (Al), tin (Sn) or zirconium (Zr) and also beta stabilizers such as beta stabilizers of the isomorphous type (e.g. vanadium (V), molybdenum (Mo), tantalum (Ta) and niobium (Nb)) and beta stabilizers of the eutectoid type (e.g. manganese (Mn), iron (Fe), chromium (Cr), cobalt (Co), nickel (Ni), and silicon (Si)). An exemplary suitable duplex titanium alloy composition is Ti-6Al-4V. The duplex alloys also include near-alpha alloy compositions which are duplex alloys having less than about two percent of beta stabilizers. Exemplary suitable near-alpha compositions include Ti-8Al-1Mo-1V and Ti-6Al-2Sn-4Zr-2Mo.

When the titanium alloy conductor according to the present invention is to be implanted in a human or animal body in contact with a polymeric insulator material which is susceptible to degradation by metal ion oxidation (MIO), the stabilizers mentioned above which could provide active metal ions that could contribute to MIO such as cobalt and molybdenum ions should be limited in the composition to less than 4% of the composition. Preferably, the composition should be substantially free of such metals.

Materials of such compositions and structure have been found to have suitable conductivity for use with implantable pulse generators or neurostimulators and suitable fatigue strength when used in endocardial lead placement. If additional conductivity is required, such as for use with an implantable defibrillator, the titanium alloy can also be provided with a core of silver or some other more conductive material in the same manner as conventional drawn brazed strand (DBS) wire. Moreover, materials having such compositions have been found to pass tests intended to detect MIO in polymeric materials.

BRIEF DESCRIPTION OF THE DRAWINGS

FIG. 1 is a plan view of a medical electrical lead system suitable for endocardial stimulation by an implantable heart pacemaker.

FIG. 1a is a cross-sectional view of a lead assembly portion of the lead system of FIG. 1.

DETAILED DESCRIPTION OF THE INVENTION

In a preferred embodiment of the present invention, a medical electrical lead comprises an electrode at a distal end thereof, a connector at a proximal end thereof and an elongated electrical conductor extending between the electrode and the connector, the conductor in electrical contact with the electrode at a distal end and in electrical contact with the connector at a proximal end, the conductor comprised of a plurality of wires or wire bundles wound in a multifilar coil configuration, the wire comprised of a duplex titanium alloy.

By duplex titanium alloy, we mean a titanium alloy having percentages of alpha stabilizers such as aluminum (Al), tin (Sn) or zirconium (Zr) and also beta stabilizers such as beta stabilizers of the isomorphous type (e.g. vanadium (V), molybdenum (Mo), tantalum (Ta) and niobium (Nb)) and beta stabilizers of the eutectoid type (e.g. manganese (Mn), iron (Fe), chromium (Cr), cobalt (Co), nickel (Ni), and silicon (Si)). An exemplary suitable duplex titanium alloy composition is Ti-6Al-4V. The duplex alloys also include near-alpha alloy compositions which are duplex alloys having less than about two percent of beta stabilizers. Exemplary suitable near-alpha compositions include Ti-8Al-1Mo-1V and Ti-6Al-2Sn-4Zr-2Mo.

The titanium alloys used in the present invention should be limited in interstitial alloying elements such as oxygen, hydrogen, nitrogen and carbon which can cause reduction in ductility which can result in failure of the conductor. In particular, during wire drawing operations (the wire is typically cold drawn with annealing processes between draws), precautions should be taken to limit the introduction of such impurities by inert atmosphere annealing (e.g. argon atmosphere) and chemical cleaning to remove oxide, scale, and other surface contaminants.

For maximum fatigue life, the wire should be in a fully hard condition. The wire in medical lead applications is typically made in round diameters ranging from about 0.004 to 0.010 although wire diameters as small as 0.001 can be used. Final chemical cleaning is typically undertaken by a soap cleaning after the final draw to remove any organic lubricants and etching with HF/HNO$_3$ to remove the dark oxide. The wire surface could, if desired, be anodized by oxidation of the wire after it is given the final chemical cleaning. The presence of such an insulating oxide layer would reduce the amount of cross-talk between wires if the insulation on the wire is breached.

A smooth surface finish for the wire is desirable. A smooth surface is easier to clean, and presents a shiny metallic finish that is aesthetically pleasing. However, typical drawn titanium alloy wire surfaces are rougher than MP35N wire used in medical leads due to the final etching step used to remove surface oxide. However, tests have not shown that the increased surface roughness adversely affects fatigue life for the material.

Figure 2A:
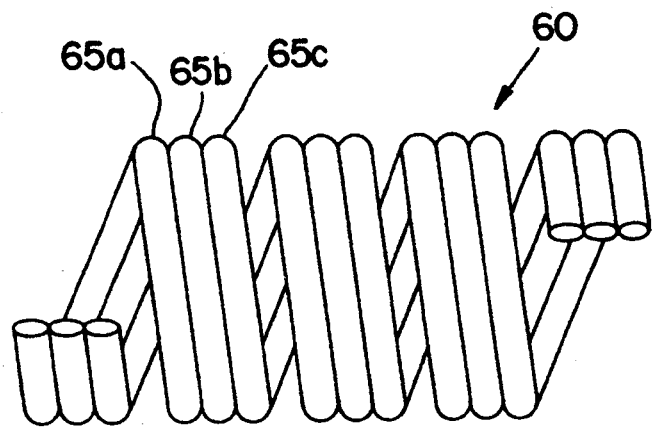
FIG. 2a is a side elevational view of a trifilar conductor winding for use in a lead conductor.
Figure 2B:
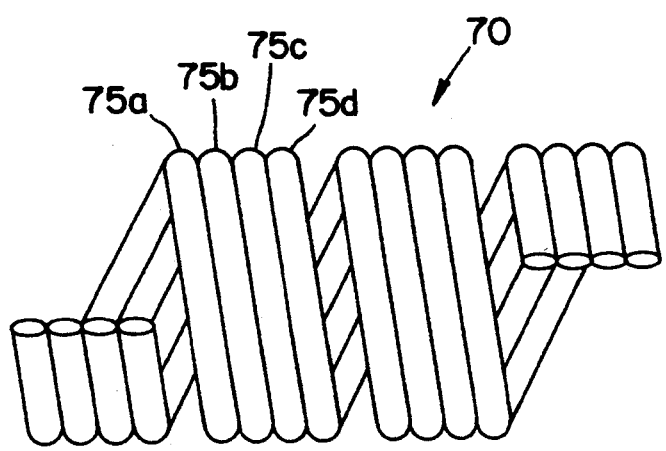
FIG. 2b is a side elevational view of a quadrafilar conductor winding for use in a lead conductor.

Referring now to the drawings, FIG. 1 shows a lead system 10 which includes a lead assembly 15, an anchoring sleeve 20, a connector 25, a stylet guide 30, and a stiffening stylet 35. Referring now to FIG. 1a, the lead assembly 15 is shown in greater detail with an electrode structure 40 at a distal end of the lead assembly 15, a tine 45 to secure the lead assembly 15 endocardially, a lead conductor 50 in a multifilar coil configuration which allows the stiffening stylet 35 to be inserted into the lead assembly 15 in the internal lumen 52 of the lead conductor 50. The lead conductor 50 is shown attached at its distal end 55 to the electrode structure 40. The lead conductor 50 is also similarly attached at a proximal end (not shown) to the connector 25. Multifilar coil configurations are also shown in FIGS. 2a and 2b in a trifilar 60 coil configuration having individual wires 65a, 65b and 65c and a quadrafilar 70 coil configuration having individual wires 75a, 75b, 75c, and 75d. Insulation elements 57a, 57b and 57c insulate portions of the electrode structure 40 and the lead conductor 50. Such insulation elements 57a, 57b, and 57c may be made from conventional silicone and polyurethane lead insulation materials. The insulator 57c is typically a hollow polymeric tube extending between the proximal and distal ends of the lead assembly 15 and insulating the lead conductor 50 from surrounding body tissues. If the polymeric insulator 57c is a material susceptible to metal ion oxidative degradation, the material of the lead conductor 50 will preferably be limited in metals that could cause MIO degradation in the insulator 57c. Metals which could contribute to MIO include manganese, iron, cobalt, nickel, chromium and molybdenum. Most preferably, the lead conductor should be substantially free of such metals. While a unipolar lead is shown, and described above, the present invention can also be applied to bipolar leads in the same manner. As used in implantable pacing leads, the individual wires of the lead conductor 50 would be typically about 0.004 to 0.010 in diameter and would be wound into extremely small coils; typically having a diameter of less than 2-3 turn.

Coiling of the titanium alloy wire to make medical leads is nearly identical to that employed in making multifilar MP35N coils except that the differences in modulus (roughly half of that in MP35N) and strength dictate the use of different mandrel size and wire tension settings that will be readily appreciated by those skilled in the art. Incorporation of the titanium alloy multifilar coil into a final lead assembly could involve the use of connector and electrode materials to which titanium alloy is weldable such as titanium, niobium, tantalum and platinum and alloys thereof or it could involve crimping the coil onto electrode and connector elements which are made from more conventional materials. In multiconductor electrodes, the wires may be provided individually with a polymeric insulation material such as silicone, polyurethane, PTFE, ETFE, polyethylene, polypropylene and other polymer coatings which can be applied by conventional means.

EXAMPLE

Selected corrosion-resistant alloys were investigated for potential use in pacemaker lead applications. The mechanical, corrosion resistance and MIO characteristics of each of these alloys was characterized and compared to those of conventional lead conductor materials, MP35N, 316L stainless steel and Elgiloy. Quadrafilar coils 0.030 inch in diameter were made from 0.005 inch diameter wire by conventional coil winding methods. The coils were subjected to coil bending fatigue tests which consisted of reverse bending of the coils about a fixed radius of curvature (i.e. at 0.084 inch and at 0.118 inch) and recording the number of cycles required to induce coil fracture. The results are as set forth in Table 1.

TABLE 1

| Alloy | Tensile Strength (KPSI) | Cycles r = 0.084" | Cycles r = 0.118" |
|---|---|---|---|
| MP35N | 290 | 14500 | 65000 |
| 316LVM | 254 | 15900 | 34100 |
| 316LVM | 239 | 14500 | 23500 |
| 316LVM | 221 | 11100 | 18600 |
| 316LVM | 186 | 9400 | 16300 |
| Elgiloy | 269 | 22600 | 59900 |
| Ti-6Al-4V | 202 | 60800 | >1000000 |
| Ti-6Al-4V | 193 | 20900 | 713700 |
| Ti-6Al-4V | 187 | 30200 | >1000000 |

The tendency of each coil material to produce metal ion oxidation (MIO) in polymers was tested in an accelerated in vitro screening test by placing the metal conductor coils into an insulator tube of the polyether urethane Pellethane 80A, tying the ends of the tube and placing the assembly in an aqueous oxidizing solution. The test sample was then stored in the test solution at 37° C. with the test solution changed three times per week. Control tubing which contained no conductor coil was used for comparison. At the end of 90 days, the qualitative visual condition of the tubing was noted and the ultimate tensile strength and elongation at break of the tubing were measured. The results of the test were as set forth in Table 2. As is shown in Table 2, the composition Ti-3Al-8V-6Cr-4Mo-4Zr, also known as Beta C (a beta titanium alloy), was shown to cause cracking in the test material while the Ti-6Al-4V duplex alloy according to the present invention did not.

TABLE 2

| Alloy | Visual | Tensile Strength (PSI) | Elongation (%) |
|---|---|---|---|
| Control | clear | 11090 | 540 |
| MP35N | cracks | 3700 | 470 |
| Elgiloy | cracks | 12600 | 570 |
| Ti-6Al-4V | clear | 12200 | 550 |
| Ti-3Al-8V--6Cr-4Mo-4Zr | cracks | 13300 | 590 |

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive concepts.

We claim:

1. A medical electrical lead comprising:
   (a) an electrode at a distal end;
   (b) a connector at a proximal end; and
   (c) an elongated electrical conductor extending between the electrode and the connector, the conductor in electrical contact with the electrode at a distal end and in electrical contact with the connector at a proximal end, the conductor comprised of a wire wound in a coil configuration, the wire comprised of a duplex titanium alloy.

2. The medical electrical lead of claim 1 wherein the coil configuration is a plurality of wires or wire bundles in a multifilar coil configuration.

3. The medical electrical lead of claim 1 wherein the titanium alloy composition includes less than 4% combined of cobalt and molybdenum.

4. The medical electrical lead of claim 1 wherein the titanium alloy composition is a duplex titanium alloy having a nominal composition of Ti-6Al-4V.

5. A medical electrical lead comprising:
   (a) an electrode at a distal end;
   (b) a connector at a proximal end;
   c) a hollow polymeric insulator extending between the proximal and distal ends, said polymeric insulator comprising a material susceptible to metal ion oxidative degradation; and
   (d) an elongated electrical conductor within the polymeric insulator and extending between the electrode and the connector, the conductor in electrical contact with the electrode at a distal end and in electrical contact with the connector at a proximal end, the conductor comprised of a wire wound in a coil configuration, the wire comprised of a duplex titanium alloy, the titanium alloy substantially free of metals that contribute to oxidative degradation in the polymeric insulator.

6. The medical electrical lead of claim 5 wherein the coil configuration is a plurality of wires in a multifilar coil configuration.

7. The medical electrical lead of claim 5 wherein the titanium alloy composition includes less than 4% combined of cobalt and molybdenum.

8. The medical electrical lead of claim 5 wherein the titanium alloy composition is a duplex titanium alloy having a nominal composition of Ti-6Al-4V.

9. The medical electrical lead of claim 5 wherein the polymeric insulator comprises a polyether urethane.

* * * * *